United States Patent [19]

Hirschberg et al.

[11] Patent Number: 5,342,400
[45] Date of Patent: Aug. 30, 1994

[54] DEFIBRILLATOR/CARDIOVERTER

[75] Inventors: Jakub Hirschberg, Taeby; Martin Obel, Danderyd, both of Sweden

[73] Assignee: Siemens Aktiengesellschaft, Munich, Fed. Rep. of Germany

[21] Appl. No.: 856,688

[22] Filed: Mar. 24, 1992

[30] Foreign Application Priority Data

Mar. 28, 1991 [DE] Fed. Rep. of Germany ....... 4110402

[51] Int. Cl.⁵ .............................................. A61N 1/39
[52] U.S. Cl. .............................................. 607/5
[58] Field of Search ........................ 128/419 D; 607/5

[56] References Cited

U.S. PATENT DOCUMENTS

| | | | |
|---|---|---|---|
| 3,359,984 | 12/1967 | Daniher et al. | 128/419 D |
| 4,168,711 | 9/1979 | Cannon, III et al. | 128/419 D |
| 4,545,203 | 10/1985 | Tacker, Jr. et al. | 128/419 D |
| 4,566,457 | 1/1986 | Stemple | 128/419 D |
| 4,821,723 | 4/1989 | Baker, Jr. et al. | 128/419 D |
| 5,111,812 | 5/1992 | Swanson et al. | 128/419 D |
| 5,163,427 | 11/1992 | Keimel | 128/419 D |

FOREIGN PATENT DOCUMENTS

| | | |
|---|---|---|
| 0326290 | 8/1989 | European Pat. Off. . |
| 3919498 | 1/1990 | Fed. Rep. of Germany . |

Primary Examiner—Angela D. Sykes
Assistant Examiner—Kennedy J. Schaetzle
Attorney, Agent, or Firm—Hill, Steadman & Simpson

[57] ABSTRACT

In order to set the current distribution of a defibrillation pulse supplied to the heart in a simple manner, a defibrillator/cardioverter has n electrodes disposed for electrically stimulating the heart, and a pulse generator for generating electrical pulses having n−1 outputs connected in series, and a total of n output terminals, to which the n electrodes are respectively connected. The pulse generator simultaneously generates an electrical pulse at each of its outputs.

8 Claims, 3 Drawing Sheets

DEFIBRILLATOR/CARDIOVERTER

BACKGROUND OF THE INVENTION

1. Field of the Invention

The present invention is directed to a defibrillator/cardioverter having a plurality of n (n being greater than or equal to three) electrodes which are connected to a means for generating electrical pulses.

2. Description of the Prior Art

A defibrillator/cardioverter is disclosed in German OS 39 19 498, wherein one of a plurality of electrodes is arranged in the interior of the heart, and the other electrodes are placed outside at the heart. Either directly, or via discharge distances which form a short-circuit for high voltages, the outer electrodes are electrically connected to each other and are connected to a first of two output terminals of the pulse generator. The electrode disposed inside the heart is connected to a second output terminal. Upon the generation of an electrical pulse as an output signal by the pulse generator, the electrical current density is distributed in the heart muscle according to the placement of the electrodes and thereby preferably penetrates the thickest zones of the heart muscle, which form the principal part of the heart muscle mass, in order to achieve successful defibrillation or cardioversion.

Another defibrillator is disclosed in U.S. Pat. No. 4,548,203, having a plurality of electrodes which are connected in pairs to different outputs of a pulse generator, and are disposed at different locations relative to the heart, which are preferably on opposite sides of the heart. For defibrillation, the individual electrode pairs are successively charged with an electrical pulse via the outputs of the pulse generator. The spatially and chronologically separated pulse output is intended to reduce the energy required for successful defibrillation.

In the aforementioned defibrillator disclosed in German OS 39 19 498, the distribution of the current in the heart can be set only on the basis of the positioning and size of the individual electrodes. The positioning of the electrodes, more specifically their spacing relative to each other and relative to the heart, is, however, limited by anatomical conditions. Moreover, an electrode is required inside the heart, and an extremely high current density arises in close proximity to this electrode, so that damage to the heart tissue is possible in the event of an unfavorable placement of this inner electrode, or a dislocation of this inner electrode.

In the defibrillator disclosed in U.S. Pat. No. 4,548,203, distribution of the current density to different zones of the heart muscle is not possible, because only two electrodes simultaneously participate in the pulse delivery.

SUMMARY OF THE INVENTION

It is an object of the present invention to provide a defibrillator or converter with which an optimum current distribution in the heart can be set for achieving an optimally low defibrillation threshold.

The above object is achieved in a defibrillator/cardioverter constructed in accordance with the principles of the present invention having a plurality of n electrodes, and pulse generator means for establishing $n-1$ output circuits connected in series. The output circuits of the pulse generator have n terminals, to which the n electrodes are respectively connected to complete those circuits. The pulse generator simultaneously generates an electrical pulse in each of the output circuits. In this arrangement, the distribution of current in the heart is not only dependent on the arrangement of the electrodes, but can also be additionally set via the electrical voltages at the outputs of the means for generating the electrical pulses. There is thus no risk of tissue damage associated with the delivery of the electrical pulses, because the pulse current can be individually set for each electrode.

As used herein an "output circuit" means an electrical current path (which includes cardiac and other intervening tissue) traversed by a current at a voltage to pass current through the heart. As a result of the distribution which is set by the electrode arrangement and the voltages, currents with respectively different voltages are simultaneously caused to pass through the heart.

In embodiment of the defibrillator/cardioverter of the invention, the pulse generator means includes $n-1$ series-connected capacitors, which are connectable to a voltage source via a switch arrangement for charging the capacitors. The terminals of the individual capacitors are connected to the output terminals of the output circuits of the pulse generator via controllable switches. As long as the switch arrangement is closed, the series capacitor circuit is charged to the charging voltage prescribed by the voltage source. The relationship of the sub-voltages across the individual capacitors, and thus the voltages at the respective output terminals of the output circuits of the pulse generator, is dependent on the capacitances of the individual capacitors, and is thus adjustable.

In order to limit the current in the event of a short circuit, inductances are preferably connected in the respective paths between the terminals of the capacitors and the output terminals of the output circuits of the pulse generator. A further advantage resulting from such inductances is that biphase current pulses, in the form of highly attenuated oscillations, are generated between the individual electrodes dependent on the value of the inductances and the electrical impedance of the heart tissue upon discharge of the capacitors. Such a pulse shape has proven particularly effective in view of the energy required for defibrillation.

In a further embodiment of a defibrillator/cardioverter of the invention, the pulse generator physically has two output poles, with a current divider circuit consisting of passive electrical components being connected between the two output poles and the n output terminals. The current divider circuit divides the defibrillation pulse from the pulse generator into different sub-pulses for the individual electrodes, with the shape and amplitude of the sub-pulses being defined by the selection and the arrangement of the passive electrical components (inductances, resistors, capacitors).

In another embodiment of the invention, the pulse generator is arranged in an implantable capsule housing and has a surface with at least regions of the surface being electrically conductive, so that those surface regions function as one of the electrodes for the defibrillator/cardioverter system. The capsule housing is implanted in the proximity of the heart for this purpose.

In the aforementioned embodiment containing a current divider circuit, the pulse generator and the current divider circuit can be respectively accommodated in separate, implantable housings connectable to each other via electrical leads. This permits existing, conventional defibrillators to be retrofitted to provide selected current distribution capability. For example, the current divider circuit in a separate housing can be implanted in a patient in whom a conventional pulse generator, which generates a defibrillation pulse between two output poles, is already implanted. Because the housing containing the current divider circuit can have smaller dimensions in comparison to the conventional housing including the pulse generator, the current divider circuit housing can be implanted in a relatively uncomplicated operation.

DESCRIPTION OF THE PREFERRED EMBODIMENTS

Figure 1:
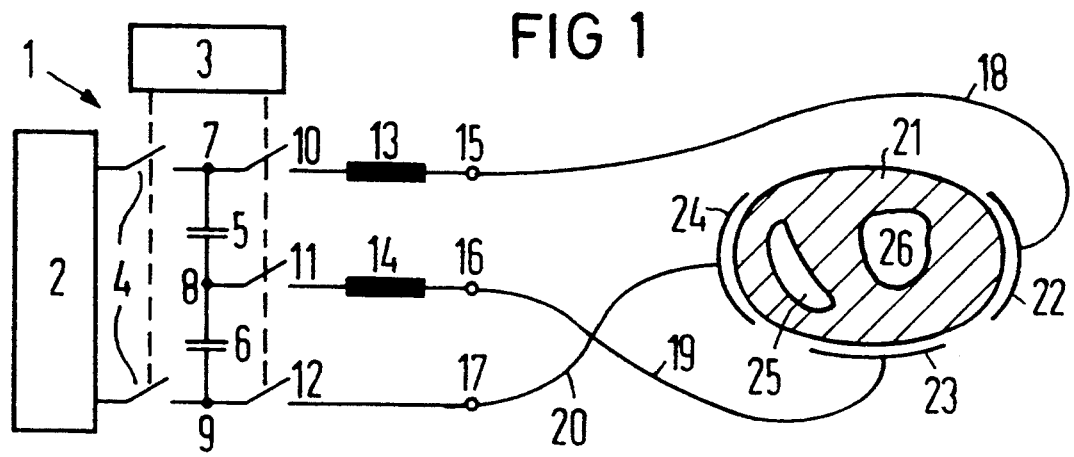
FIG. 1 is a schematic circuit diagram of a first embodiment of a defibrillator/cardioverter constructed in accordance with the principles of the present invention, shown connected to a heart.

In FIG. 1, the reference numeral 1 designates generally a means for generating electrical pulses (pulse generator). The pulse generator 1 contains a voltage source 2, which can be connected across two capacitors 5 and 6 connected in series, via a switch arrangement 4 controllable by a control unit 3. The series circuit of the capacitors 5 and 6 has three different terminal locations 7, 8 and 9, which are respectively connected to output terminals 15, 16 and 17 of the pulse generator 1 through controllable switches 10, 11 and 12, and through respective inductances 13 and 14 in the case of the terminal locations 7 and 8. The controllable switches 10, 11 and 12 can be simultaneously driven by the control unit 3.

The output terminals 15, 16 and 17 established two series-connected output circuits of the pulse generator 1, this number (two) corresponding to the number of series-connected capacitors. The two output circuits of the pulse generator 1 are connected via electrode lines 18, 19 and 20 to respective electrodes 22, 23 and 24 arranged at a heart 21, shown in cross section, to complete the output circuits by creating respective current paths through the heart 21. In the illustrated exemplary embodiment, the number of electrodes can be expanded to n (n being greater than or equal to two) without difficulty, with n−1 capacitors in series establishing n−1 output circuits with n output terminals for the n electrodes.

As long as the switch arrangement 4 is closed, the series circuit of the capacitors 5 and 6 is charged to the charging voltage prescribed by the voltage source 2, with the sub-voltages across the individual capacitors 5 and 6 being dependent on their capacitance. For defibrillation of the heart 24, the switches 10, 11 and 12 are simultaneously closed, so that the capacitors 5 and 6 are discharged via the inductances 13 and 14 as well as via the heart tissue disposed between the electrodes 22, 23 and 24. Current pulses are thus respectively simultaneously supplied to the heart 21 via the electrodes 22, 23 and 24. The respective pulse amplitude and energy content of these current pulses are dependent on the sub-voltages across the capacitors 5 and 6, the values of the inductances 13 and 14, and the respective impedances of the current paths formed by the heart tissue between the electrodes 22 and 23, the electrodes 23 and 24, and the electrodes 22 and 24. Due to the presence of the inductances 13 and 14, the current pulses have the shape of a biphase, highly attenuated oscillation, which is especially beneficial for achieving effective defibrillation. The inductances 13 and 14 also serve to limit the current in the event of a short-circuit fault in the pulse generator 1.

As is schematically indicated in FIG. 1, the heart muscle mass is non-uniformly distributed over the cross section of the heart 21. If a standardized value of "one" is set for the thickness of the heart muscle between the right ventricle 25 and the neighboring outside wall of the heart, the heart muscle mass between the right ventricle 25 and the left ventricle 26 will have a value of approximately "two," and the heart muscle mass between the left ventricle 26 and the outside wall of the heart in the region of the electrode 22 will have a value of approximately "three." The heart muscle mass between the left ventricle 26 and the outside wall of the heart in the region of the electrode 23 will also have a value of approximately "two." If the capacitance relationships of the capacitors 5 and 6 are selected so that the voltage across the capacitor 5 is approximately two-thirds of the magnitude of the total voltage across the terminal locations 7 and 9, and the voltage across the capacitor 6 is approximately one-third of the total voltage magnitude, a distribution of the current which uniformly covers all regions of the heart muscle will be achieved, and the energy required for defibrillation will be reduced to approximately 60 through 80% of the energy required for achieving defibrillation in a system having only two electrodes.

The exemplary embodiment shown in FIG. 1 can be an embodied in an implantable or in a non-implantable defibrillator/cardioverter. Accordingly, the electrodes 22, 23 and 24 can be arranged at the heart 21 in vivo, or can be arranged on the body surface of the patient in an appropriate arrangement relative to the heart 21.

Figure 2:
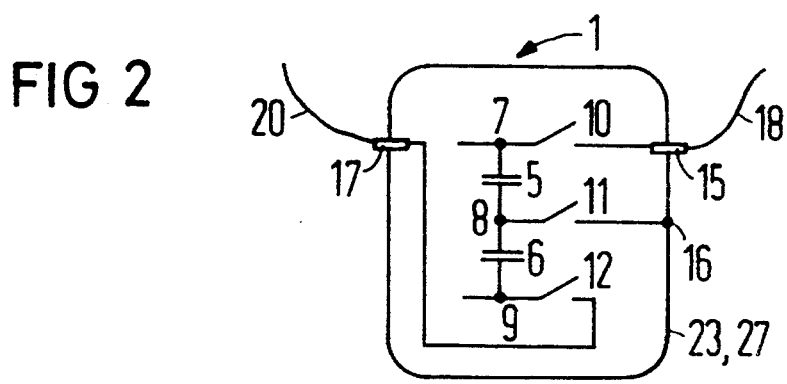
FIG. 2 is a schematic circuit diagram of a portion of the defibrillator/cardioverter constructed in accordance with the principles of the present invention in an implantable housing which assumes the function of one electrode.
Figure 3:
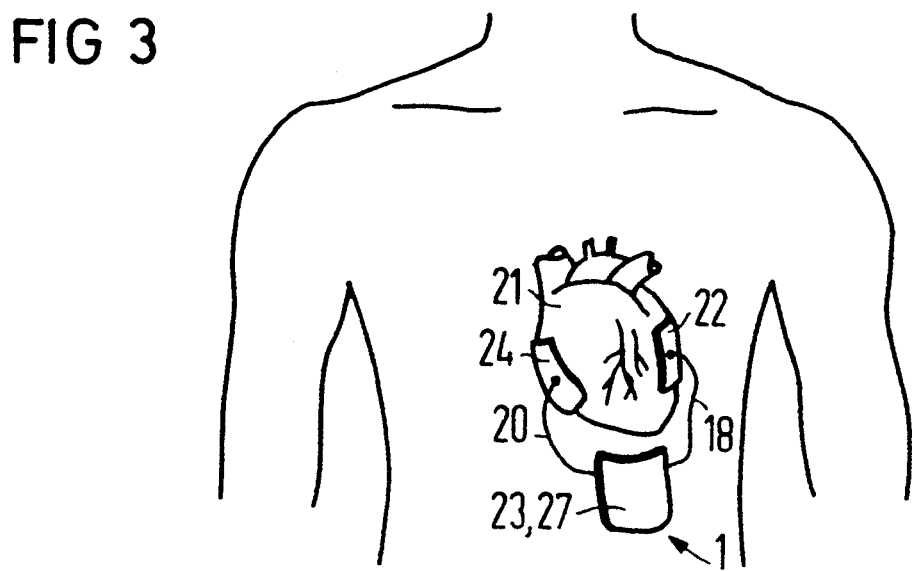
FIG. 3 shows the arrangement of the defibrillator/cardioverter of FIG. 2, with two further electrodes in the human body.

An exemplary embodiment of a pulse generator 1 is shown in FIG. 2 in an implantable capsule housing 27, preferably consisting of titanium. For simplifying the illustration, only the two capacitors 5 and 6 and the controllable switches 10, 11 and 12 are shown inside the capsule housing 27. The output terminals 15 and 17 connected to the terminal locations 7 and 9 are in the form of insulated bushings through the metal housing 27. As can be seen in FIG. 3, electrode leads 18 and 20 are connected to these output terminals, the leads 18 and 20 respectively terminating in electrodes 22 and 24 applied directly to the heart 21. The terminal location 8 between the capacitors 5 and 6 is connected via the switch 11 directly to the metal housing 27, so that the metal housing 27 assumes the function of the electrode 23 discussed above, as also indicated in FIG. 3.

Figure 4:
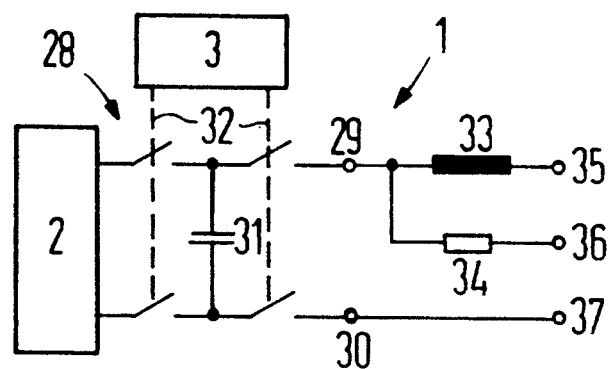
FIG. 4 is a schematic circuit diagram of a further embodiment of a defibrillator/cardioverter constructed in accordance with the principles of the present invention, including a current divider circuit.

A further embodiment of a defibrillator/cardioverter of the invention is shown in FIG. 4, wherein the means for generating electrical pulses is in the form of a pulse generator 28 having two output poles 29 and 30. The pulse generator 28 is constructed in the manner of a conventional defibrillator, and contains a capacitor 31 which can be switched by a switching arrangement 32, controlled by a control unit 3, so that the capacitor 31 will either be charged by a voltage source 2, or will generate a defibrillation pulse as an output at the two output poles 29 and 30 of the pulse generator 28. The two output poles 29 and 30 are connected to the three output terminals 35, 36 and 37 of the overall means for generating pulses 1 via a current divider circuit consisting of passive electrical components. In the embodiment of FIG. 4, the current divider circuit is formed by an inductance 33 and a resistor 34. Corresponding to the arrangement of FIG. 1, the output terminals 35, 26 and 37 are connected to leads (not shown) which terminate in electrodes for the delivery of stimulation pulses to the heart.

Figure 5:
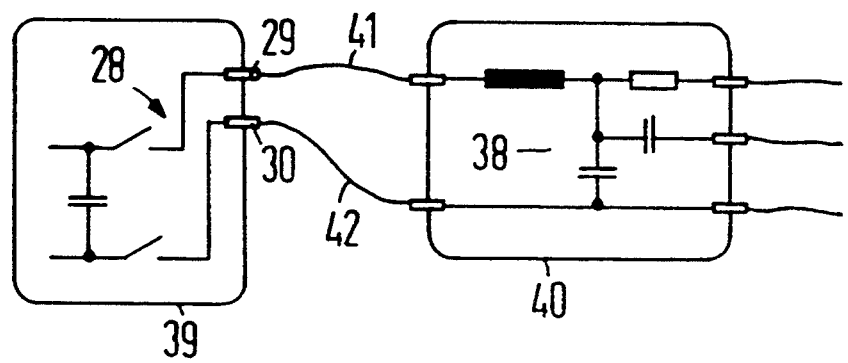
FIG. 5 is a schematic circuit diagram showing the embodiment of FIG. 4 with the pulse generator and the current divider circuit in separate, implantable housings.

In the embodiment of FIG. 5, the pulse generator 28 and the current divider circuit 38 are respectively accommodated in two separate, implantable housings 39 and 40, which are connected to each other via electrical leads 41 and 42. This embodiment permits conventional defibrillators (corresponding to the pulse generator 28 by itself) which may be "on the shelf" or already implanted, to be retrofitted in accordance with the principles of the present invention so as to be able to provide an output of different current pulses at a plurality of electrodes. Because the separate housing 40 can have smaller dimensions in comparison to the housing 39, the housing 40 can be implanted in the body of a patient in addition to the existing pulse generator 28 in a relatively uncomplicated operation.

In accordance with the embodiment shown in FIG. 2, the housing 40 containing the current divider circuit 38 can also be fashioned as an electrode. Moreover, the selection and arrangement of the passive components shown in FIGS. 4 and 5 will be understood as being but one example of many other possible combinations.

Figure 6:
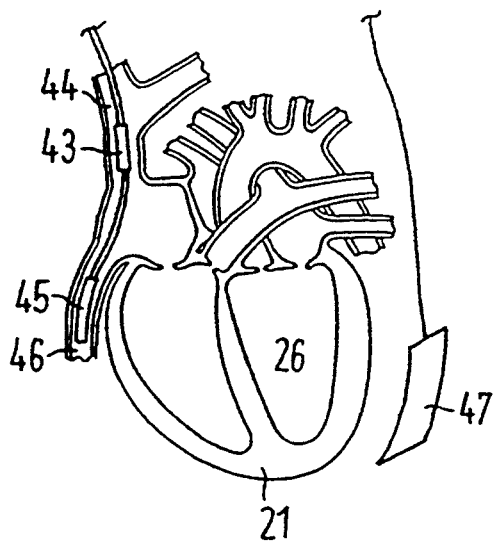
FIGS. 6, 7 and 8 show various examples for positioning the electrodes in the defibrillator/cardioverter constructed in accordance with the principles of the present invention.
Figure 7:
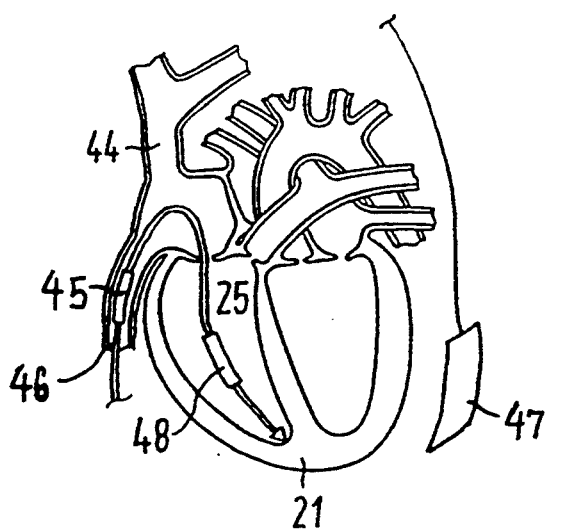
Figure 8:
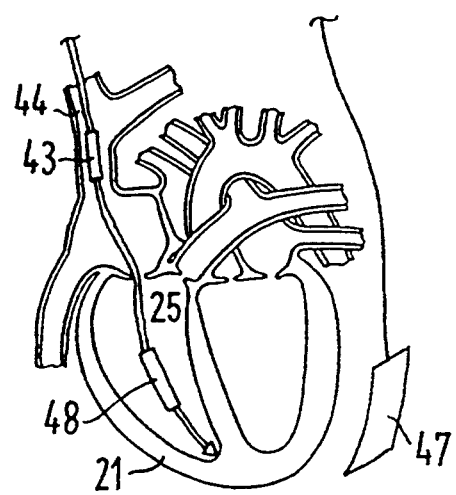

Three further examples for arranging the electrodes with respect to the heart 21 are shown in FIGS. 6, 7 and 8. In the embodiment of FIG. 6, a first electrode 43 is disposed in the superior vena cava 44, a second electrode 45 is disposed in the inferior vena cava 46, and a third planar (patch) electrode 47 is disposed opposite the left ventricle 26 of the heart 21, preferably subcutaneously. As used herein, "subcutaneously" means that the electrode is implanted just beneath the skin surface, rather than by invasive surgery to the thoracic cavity. In the embodiment of FIG. 6, no electrode is disposed inside the heart, which is advantageous for patients having a hypersensitive heart, for example a patient who has recently had a cardiac infarction.

In the embodiment of FIG. 7, an electrode 48 is disposed in the right ventricle 25 of the heart 21, instead of in the superior vena cava 44. The other electrodes 45 and 47 are placed as described above in connection with the embodiment of FIG. 6.

In the embodiment of FIG. 8, the electrode 43 in the superior vena cava 44 is provided in combination with the electrode 48 in the right ventricle 25, and in combination with subcutaneous planar electrode 47.

Although modifications and changes may be suggested by those skilled in the art, it is the intention of the inventors to embody within the patent warranted hereon all changes and modifications as reasonably and properly come within the scope of their contribution to the art.

We claim as our invention:

1. A defibrillator/cardioverter comprising:
   pulse generator means for generating electrical pulses;
   a plurality of n electrodes, n being greater than or equal to three, for delivering said electrical pulses to the heart of a patient;
   said pulse generator means including means for establishing n−1 series-connected output circuits having a total of n output terminals, said pulse generator means simultaneously generating an electrical pulse in each of said n−1 series-connected output circuits; and
   means for respectively electrically connecting said n output terminals to said n electrodes to complete said n−1 series-connected output circuits.

2. A defibrillator/cardioverter as claimed in claim 1, wherein said pulse generator means includes n−1 series-connected capacitors having n capacitor terminals, a voltage source, a first switch arrangement connected between said voltage source and said capacitors, a second switch arrangement connected between said terminals of said capacitors and said output terminals, and control means for controlling said first and second switch arrangements for either connecting said capacitors across said voltage source for charging said capacitors or for connecting said terminals of said capacitors to said output terminals.

3. A defibrillator/cardioverter as claimed in claim 2 further comprising a plurality of inductances respectively connected between at least some of said terminals of said capacitors and said output terminals.

4. A defibrillator/cardioverter as claimed in claim 1 wherein said pulse generator means comprises a pulse generator having two output poles and a current divider circuit consisting of a plurality of passive electrical components connected between said two output poles of said pulse generator and said n output terminals.

5. A defibrillator/cardioverter as claimed in claim 4 further comprising a first housing for in vivo implantation in a patient containing said pulse generator, and a second housing for in vivo implantation in said patient containing said current divider circuit, and electrical leads extending between said first and second housings electrically connecting said pulse generator and said current divider circuit.

6. A defibrillator/cardioverter as claimed in claim 5 wherein said second housing has a surface having at least a region thereof consisting of electrically conductive material forming one of said electrodes.

7. A defibrillator/cardioverter as claimed in claim 5 wherein said first housing has a surface having at least a region thereof consisting of electrically conductive material forming one of said electrodes.

8. A defibrillator/cardioverter as claimed in claim 1 wherein said pulse generator means is contained in a housing for in vivo implantation in patient, said housing having a surface with at least a region thereof consisting of electrically conductive material forming one of said electrodes.

* * * * *